United States Patent
Birkhoff et al.

(10) Patent No.: US 7,381,854 B2
(45) Date of Patent: Jun. 3, 2008

(54) SELECTIVE HYDROGENATION OF ALPHA-METHYL-STYRENE TO CUMENE

(75) Inventors: Ronald Birkhoff, Spring, TX (US); Clive Griffiths, Wilmslow (GB); Kiran Shah, Sugar Land, TX (US); Anand Subramanian, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 739 days.

(21) Appl. No.: 10/905,177

(22) Filed: Dec. 20, 2004

(65) Prior Publication Data

US 2006/0135830 A1   Jun. 22, 2006

(51) Int. Cl.
*C07C 5/11* (2006.01)
*C07C 5/10* (2006.01)

(52) U.S. Cl. .................. 585/265; 585/258; 585/266
(58) Field of Classification Search ........... 585/258, 585/265, 266
See application file for complete search history.

(56) References Cited

U.S. PATENT DOCUMENTS

| | | | |
|---|---|---|---|
| 3,290,384 A | 12/1966 | Largman et al. | 260/610 |
| 3,646,235 A | 2/1972 | Little et al. | 260/667 |
| 4,410,755 A | 10/1983 | Fisher et al. | 585/800 |
| 4,822,936 A | 4/1989 | Maurer et al. | 585/259 |
| 5,064,507 A | 11/1991 | O'Donnell et al. | 203/34 |
| 5,430,200 A | 7/1995 | Hood | 568/798 |
| 5,905,178 A | 5/1999 | Hildreth | 585/258 |

OTHER PUBLICATIONS

"Phenol"; Kellogg Brown & Root, Inc.; 2000.

*Primary Examiner*—Thuan Dinh Dang
(74) *Attorney, Agent, or Firm*—KBR IP Legal Dept.

(57) ABSTRACT

A process for the selective hydrogenation of alpha-methylstyrene (AMS) to cumene in a two catalyst system is disclosed. A crude cumene feed stream containing up to 10% AMS by weight is supplied to the first reaction zone 112 and mixed with hydrogen in a first catalyst bed 118 containing a nickel catalyst, converting from 70 to 95 percent of the AMS to cumene. Cumene and remaining AMS are separated from hydrogen in a liquid take off tray 120. The first reaction zone 112 effluent is supplied to a second reaction zone 114, where the effluent and hydrogen gas are mixed in a second catalyst bed 126 containing a noble-metal catalyst to substantially convert any remaining AMS to cumene. Cumene is collected, separated from the hydrogen, and can be resupplied to the hydrogenation reactor 110, or supplied as feed to a phenol synthesis loop.

25 Claims, 1 Drawing Sheet

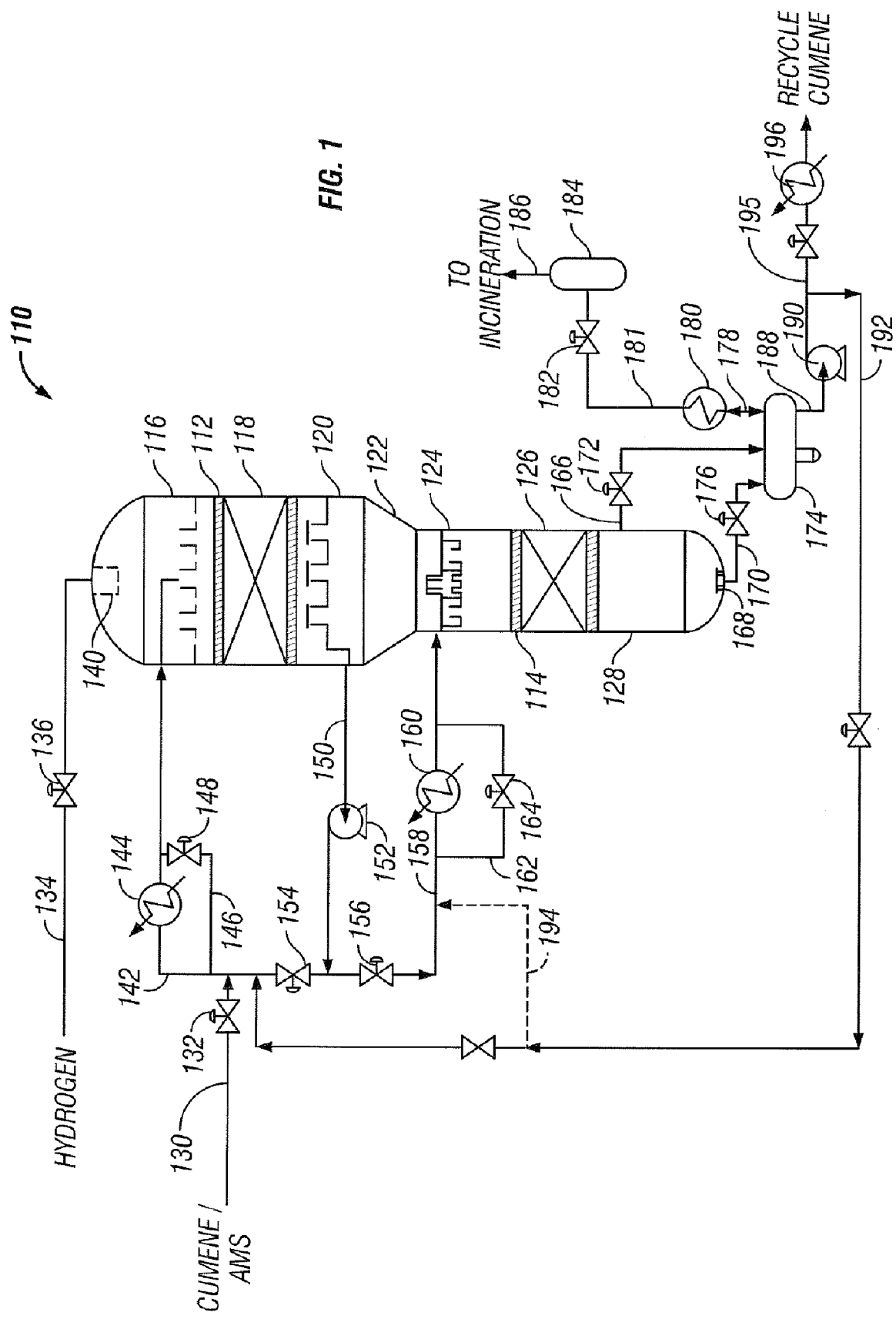

SELECTIVE HYDROGENATION OF ALPHA-METHYL-STYRENE TO CUMENE

BACKGROUND OF THE INVENTION

This invention relates to the selective hydrogenation of alpha-methyl-styrene (AMS) to cumene, and more particularly to the selective hydrogenation of alpha-methyl-styrene to cumene using a combination of a nickel catalyst and a noble-metal catalyst to achieve an optimal combination of conversion and selectivity at a lower overall catalyst volume and cost.

The production of phenol from cumene by the KBR Phenol Process has been studied for more than 50 years. Typically, cumene can be oxidized with air to produce cumene hydroperoxide (CHP), which can be concentrated and cleaved to produce phenol and acetone in the presence of an acid catalyst using, for example, the KBR Advanced Cleavage System. The catalyst can be removed, and the mixture can be fractionated to produce high-purity products, principally phenol and acetone. The fractionation train can be designed to separate alpha-methyl-styrene (AMS) as co-product, or the AMS can be hydrogenated to cumene for recycle to the oxidation step. Representative patents disclosing the production of phenol from cumene via cleavage of the hydroperoxide include U.S. Pat. No. 3,290,384 to Largman, U.S. Pat. No. 3,646,235 to Little and U.S. Pat. No. 5,430,200 to Hood.

AMS is an inevitable by-product of the cumene-to-phenol process. AMS precursors can be formed in the cumene oxidation step, and converted to AMS during the subsequent cleavage step. AMS is generally viewed as an undesired reaction by-product due to difficulty in removing AMS from both the phenol in the rectification step and from the recycled cumene stream, and due to a relatively small market for AMS. When market conditions dictate, AMS can be separated, purified and exported for sale. AMS produced in the synthesis of phenol can also be hydrogenated to cumene and recycled to the oxidation step to enhance the overall yield of the phenol process.

Hydrogenation of AMS has previously been disclosed using noble-metal catalysts, notably palladium (Pd) on alumina ($Al_2O_3$) or carbon support, where the catalyst can be used in a fixed bed system in the liquid phase, or in a trickle bed system with both vapor and liquid phases. In U.S. Pat. No. 3,646,235, Little et al. disclose the use of nickel, platinum, palladium, cobalt, chromium oxide and mixed metal catalysts for the hydrogenation of AMS. A palladium catalyst having a metal content of between 1 and 5% is noted as being preferred, for use at temperatures of 24°-120° C. (75°-248° F.) and pressures of 0.17-0.86 MPa (25-125 psia), preferably at temperatures of 24°-50° C. (75°-122° F.) and pressures of 0.17-0.45 MPa (25-65 psia).

In U.S. Pat. No. 4,822,936, Maurer et al. disclose selective hydrogenation of phenylacetylene, in the presence of styrene, with a copper catalyst supported on gamma alumina. The use of palladium catalysts is discussed, but is discouraged due to the large excess of hydrogen required, often resulting in the hydrogenation of styrene.

In U.S. Pat. No. 5,064,507, O'Donnell et al. disclose a process for the purification of a crude phenol stream having between 0.5 and 10 weight percent AMS present by separating AMS from the crude phenol product using a steam distillation process.

In U.S. Pat. No. 5,905,178, Hildreth discloses the removal of AMS from cumene by selective hydrogenation of the side chain in a distillation column reactor. The process includes the step of contacting the cumene/AMS feed stream with hydrogen and catalyst material, with the catalyst specified as preferably being palladium oxide on an appropriate support. The reaction feed is given as 18 weight percent AMS and 82 weight percent cumene, with the catalyst zone being maintained at a pressure and temperature of 0.21 MPa (30 psia) and 174° C. (345° F.), respectively.

Hydrogenation of AMS has previously been disclosed using Raney nickel catalysts in a slurry process, but the process has been largely replaced with the fixed bed process due to loss of aromatics. Although the slurry process is effective, it requires two distillation towers and associated equipment, as well as energy in the form of cooling and pressure. Additionally, the Raney nickel-based catalysts have drawbacks, including producing undesired side products due to over-hydrogenation, and a need for frequent addition of fresh catalyst.

Noble metal hydrogenation catalysts typically can exhibit high conversion yields and selectivity, as well as long catalyst life with little need for regeneration. However, noble metal catalysts are generally substantially more expensive than typical nickel catalysts.

The present invention can provide a mixed catalyst system for the hydrogenation of AMS to cumene that takes advantage of the low cost and high activity of the nickel catalyst and the high selectivity and long catalyst life of the noble metal catalyst.

SUMMARY OF THE INVENTION

The present invention is directed to the selective hydrogenation of alpha-methyl-styrene to cumene using a combined catalyst system having a nickel-based catalyst and a noble-metal catalyst.

The present invention provides, in one embodiment, a process for the selective hydrogenation of alpha-methyl-styrene (AMS) to cumene. The process includes contacting a feed stream comprising AMS in cumene with nickel in the presence of hydrogen in a first fixed bed catalytic reaction zone to convert from 70 to 95 percent of the AMS to cumene, and contacting effluent from the first zone with a noble group metal in the presence of hydrogen in a second fixed bed catalytic reaction zone to convert AMS in the first zone effluent to obtain a net reactor effluent comprising cumene essentially free of AMS.

The feed stream can comprise less than 6 weight percent AMS. The nickel in the first reaction zone can be fixed on an inert support. The process can further include recirculating a portion of the first zone cumene effluent to the cumene feed stream, optionally with cooling for temperature control of the first zone. The process can further include supplying the hydrogen to the first zone at a molar hydrogen:AMS ratio of from stoichiometric to 100 percent excess hydrogen. The unreacted hydrogen can be passed from the first reaction zone to the second reaction zone. The beds of the first and second reaction zones can be disposed in a common reactor vessel. The first reaction zone can have a liquid hourly space velocity from 10 to 20 per hour. The second reaction zone can include supported palladium catalyst and can have a liquid hourly space velocity of from 5 to 15 per hour. The first reaction zone can have an average temperature between 60° and 90° C. (140 to 194° F.). Isopropylcyclohexane (IPCH) formation in the first reaction zone effluent can be minimized so that the first zone effluent is essentially free of IPCH, for example, not more than 50 ppmw IPCH. The net reactor effluent can include less than 750 ppmw AMS. Desirably, the reactor effluent can include less than 300 ppmw AMS.

The present invention also provides an improvement to the process for the selective hydrogenation of AMS over a noble group metal in the presence of hydrogen to obtain a cumene product comprising less than 750 ppmw AMS. The improvement includes contacting a feed stream comprising up to 6 weight percent AMS in cumene in the presence of hydrogen with supported nickel catalyst in a fixed bed upstream from the supported noble group metal catalyst to convert from 70 to 95 percent of the AMS to cumene in an intermediate stream that can be essentially free of IPCH, and supplying the intermediate stream with hydrogen to a downstream fixed bed comprising the supported noble group metal catalyst to obtain a stream of the cumene product comprising less than 750 ppmw AMS.

The improvement can further include recirculating a portion of the intermediate stream to the feed stream optionally with cooling for temperature control of the upstream fixed bed. The improvement can further include supplying the hydrogen to the upstream fixed bed at a molar ratio to the AMS in the feed stream from stoichiometric to 100 percent excess hydrogen. The unreacted hydrogen can be passed from the upstream fixed bed to the downstream fixed bed. The upstream and downstream fixed beds can be disposed in a common reactor vessel. The upstream bed can have a liquid hourly space velocity from 10 to 20 per hour. The downstream bed can include supported palladium catalyst and can have a liquid hourly space velocity of from 5 to 15 per hour. The upstream bed can have an average temperature between 60° and 90° C. (140 to 194° F.). Since IPCH formation can be minimized, the intermediate stream can be essentially free of IPCH, for example, not more than 50 ppmw IPCH.

In another embodiment, the invention provides an apparatus for selective hydrogenation of AMS to cumene. The apparatus includes reactor means for contacting a feed stream comprising AMS in cumene with nickel in the presence of hydrogen in a first fixed bed catalytic reaction zone for converting from 70 to 95 percent of the AMS to cumene; and reactor means for contacting effluent from the first zone with a noble group metal in the presence of hydrogen in a second fixed bed catalytic reaction zone to convert AMS in the first zone effluent for obtaining a net reactor effluent comprising cumene essentially free of AMS.

BRIEF DESCRIPTION OF THE DRAWINGS

FIG. 1 is a schematic diagram of a two-catalyst bed reactor for the hydrogenation of alpha-methyl-styrene to cumene, wherein the first catalyst bed includes a nickel catalyst and the second catalyst bed includes a noble metal catalyst, according to one embodiment of the invention.

DESCRIPTION OF THE INVENTION

Detailed embodiments of the present invention are disclosed herein. However, it is understood that the disclosed embodiments are merely exemplary of the invention, which can be embodied in various forms. Specific structural, functional, and operational details disclosed herein are not intended to be limiting, but are merely illustrations that can be modified within the scope of the attached claims.

The present invention provides a method for the selective hydrogenation of alpha-methyl-styrene (AMS), which is typically produced as an undesired by-product during the synthesis of phenol from cumene. Typically, AMS produced in the synthesis of phenol is present in the crude cumene stream in a concentration of approximately 1-10 weight percent, depending upon operating conditions. In the present invention, the crude cumene stream containing AMS can be supplied to a hydrogenation reactor, hydrogenated over a two-bed nickel and noble metal catalyst system to produce a cumene stream which is substantially AMS free. The cumene stream can then be recycled as a feed stream for the synthesis of phenol. The majority of the hydrogenation takes place in the nickel catalyst bed, with the remaining AMS being hydrogenated in the noble metal catalyst bed. The two part catalyst system results in reduced overall catalyst volume, reduced capital expenses, and reduced operating expenses.

Referring to FIG. 1, a hydrogenation reactor 110 for the hydrogenation of AMS in a cumene stream over a two catalyst bed system is shown. The reactor 110 can consist of a first reaction zone 112 and a second reaction zone 114, where the first reaction zone 112 can contain a nickel catalyst and the second reaction zone 114 can contain a noble metal catalyst. The first and second reaction zones 112, 114 can be contained in separate reactors, or desirably can be contained within the same reactor shell.

The first reaction zone 112 can have a distributor 116 for mixing the liquid and gaseous components, a first catalyst bed 118 comprising a trickle bed with a nickel-based catalyst for hydrogenation of AMS, and a liquid take off tray 120. The liquid take off tray 120 can include a series of plates and channels that can channel the liquid feed to a first reaction zone outlet while allowing the unreacted hydrogen gas to pass directly though a transition section 122 and into the second reaction zone 114.

The second reaction zone 114 can include a second distributor 124, a second catalyst bed 126 comprising a trickle bed with a noble metal catalyst, and a collection space 128. The collection space 128 can include a first outlet for removal of liquid product and a second outlet for the removal of excess hydrogen gas.

While the embodiment of the reactor described above features trickle beds for the hydrogenation of AMS, it is understood that other embodiments of the present invention can feature alternate catalyst bed configurations. For example, the reactor can be configured to use a fixed bed catalyst reactor wherein the hydrogen and cumene/AMS feed can be supplied to the reactor in co-current upflow or down flow modes.

The first catalyst bed 118 desirably contains a nickel catalyst and can be any generally commercially available nickel hydrogenation catalyst demonstrating good selectivity for the hydrogenation of the ethylenic side group of AMS, without the unwanted side effect of loss of aromaticity. The nickel catalyst can be supported or unsupported, and can contain between 0.1 and 50 percent nickel by weight, with the remainder of the weight being made up by the support material. Desirably, the nickel content of the catalyst is between 10 and 25 weight percent. In the case of the supported catalyst, the support material can include, for example, silica, titania, zirconia, alumina, keiselguhr, magnesia, calcium aluminate cements, other inorganic carriers, carbon, and other known materials.

The catalyst can be provided in any suitable form, desirably with a minimum dimension of at least 1 mm. Specific particle dimensions can be selected based upon reaction conditions and the type of catalyst bed being used. The catalyst can include any shape providing sufficient surface area, including but not limited to, cylinders, tablets, granules, spheres, lobed cylinders, or combinations thereof. The catalyst can also contain holes or passages. The particles can be formed by methods known in the art, such as, for example, extrusion or tabletting, or the like. The catalyst can be shaped either before the nickel and/or any promoter compounds are introduced, or it can be shaped after manufacture of the materials. The catalyst can be supplied as a nickel oxide catalyst, which can then be reduced to nickel in the process, or the nickel component of the catalyst can be pre-reduced and metal surface passivated.

One example of a suitable nickel hydrogenation catalyst is commercially available under the trade designation HTC NI 405 RP produced by Johnson Matthey. HTC NI 405RP, for example, is a trilobe extrudate nickel catalyst on an alumina support with a surface area approximately 1 $m^2/g$. The catalyst can have a nominal size of 1.2 mm, and a nickel content of approximately 16 weight percent. Generally, the catalyst can be manufactured in a reduced and passivated form, and reduced with hydrogen at moderate temperatures to activate the catalyst.

The second catalyst bed 126 can contain a noble-metal catalyst, with a relatively high activity and a good selectivity to hydrogenation of the ethylenic side group of the AMS without loss of aromaticity. The metal can be selected from the group consisting of, but not limited to, platinum, palladium, iridium, rhodium, osmium, ruthenium, and so on, and can be on a support material. The support material can be selected from silica, titania, zirconia, alumina, keiselguhr, magnesia, calcium aluminate cements, other inorganic supports, carbon, or other suitable materials. The catalyst desirably can have a minimum dimension of at least 1 mm, and can be shaped in the form of cylinders, tablets, spheres, granules, lobed cylinders, or other shapes, and can have passages or holes as desired.

Metal content in the catalyst can be between 0.1 and 50 percent metal by weight, with the remainder being support material. Desirably, the catalyst has between 0.1 and 10 percent metal by weight. The metal group can be introduced to the catalyst support material by any suitable method known to those skilled in the art. For example, the support material can be impregnated with a solution of a soluble metal salt. After impregnation, the support can be dried and subjected to treatment at high temperatures to convert the impregnated metal to an oxide species. In the case of palladium, the support can be impregnated with a solution of palladium nitrate or palladium chloride, which can then be converted to the metal oxide by being subjected to treatment at high temperatures.

An example of a palladium catalyst suitable for use in the second catalyst bed is the hydrogenation catalyst available under the trade designation 309/6 E manufactured by Johnson Matthey. The 309/6 E palladium catalyst demonstrates high selectivity for hydrogenation of the ethylenic side group without loss of aromaticity due to over hydrogenation of the aromatic ring. The 309/6 E catalyst can have a trilobe shape on an alumina base with a nominal size of approximately 2.5 mm, and a surface area of approximately 110 $m^2/g$. The palladium content can be approximately 0.3 percent by weight. The catalyst can be manufactured in the oxide form and can be activated using hydrogen.

To hydrogenate the AMS, a cumene feed containing up to 10 percent AMS by weight can be supplied to the hydrogenation reactor 110 via line 130. The feed can be a crude stream taken from a phenol synthesis process which, in addition to cumene and AMS, can also include lighter and heavier aromatics. Desirably, the reactor feed mixture contains between 2 and 6 weight percent AMS, and even more desirably, the feed mixture contains approximately 4 weight percent AMS. The AMS content of the feed stream can be used to control the temperature rise of the hydrogenation reaction, more AMS in the feed generally resulting in a higher temperature rise. Feed supply line 130 can include a flow control valve 132 to control the rate of the feed stream.

Hydrogen gas can be supplied to the first reaction zone 112 of the reactor via line 134 which can include a flow control valve 136. Hydrogen can be supplied at a hydrogen: AMS ratio from a stoichiometric amount up to a 10-fold molar excess. Desirably, the hydrogen is supplied at a hydrogen:AMS ratio from a stoichiometric amount to a 100 percent hydrogen excess. Hydrogen enters the first reaction zone 112 through an inlet, which can contain a hydrogen distributor 140 or other dispersion device. The hydrogen inlet can be located at the top of the reactor shell, and is desirably upstream from the cumene/AMS feed inlet.

The liquid cumene/AMS feed mixture can be supplied to line 142, which can then supply the first reaction zone 112. Line 142 can include a heat exchanger 144 to heat or cool the feed stream 142 as desired. A bypass line 146 can include a flow control valve 148, allowing a portion of the cumene/AMS feed to bypass the heat exchanger 144. The bypass line 146 and valve 148 can be used to control the temperature of the feed to the reactor. The cumene/AMS feed can be supplied to the reactor inlet, where the feed enters the distributor section 116 of the reactor and mixes with hydrogen gas.

The hydrogen and liquid feed contact a distributor 116 which facilitates mixing of the cumene/AMS feed and the hydrogen gas. Hydrogenation of the AMS can occur in the trickle bed 118 having a nickel catalyst, as previously described. A cumene-rich product stream and the unreacted hydrogen gas exit the catalyst bed 118, and are separated in a liquid take off section 120. The cumene-rich product stream can include between 5 and 30 percent of the initial AMS. Hydrogenation of the AMS in the first catalyst bed is desirably at a conversion of between 70 and 95 percent of the initial feed.

The liquid take off section 120 features a series of plates that channel the liquid cumene and remaining AMS exiting the nickel catalyst bed 118 to a first reaction zone outlet which is fed to line 150. Unreacted hydrogen gas passes directly from the first catalyst bed 118 through the liquid take off section 120 to the second catalyst section 114 though a connecting space 122.

The cumene-rich stream, having a reduced AMS content, exits via line 150, which can contain a pump 152. Line 150 supplies the cumene-rich stream to line 142. Line 142 can include flow control valves 154 and 156 which can allow the cumene-rich stream to be recycled to the first reaction zone 112, or supplied to the second reaction zone 114, in whole or in part.

Line 142 connects to line 158 downstream of valves 154, 156, and can supply feed directly to the second reaction zone. Line 158 can include a heat exchanger 160, allowing the feed to be heated/cooled as desired. Line 158 can also include a bypass line 162, which can include a valve 164, allowing a portion of the cumene-rich stream to bypass the heat exchanger 160. The temperature of the feed can be controlled by allowing a portion of the feed to bypass the heat exchanger.

The cumene-rich feed stream enters the second reaction zone 114 via an inlet located upstream from the distributor 124, where it mixes with hydrogen which flows from the first reaction zone 112, through a transition section 122. If desired, a second mixing device (not shown) can be added to the distributor 124 to assist in mixing of the feed stream and the hydrogen. The hydrogen and cumene-rich feed mixture is supplied to a second catalyst bed 126, where hydrogenation of any AMS remaining in the cumene-rich stream can occur. The second catalyst bed 126 desirably contains a noble metal catalyst, as previously described. The product stream from the second catalyst bed 126, containing cumene and desirably only trace amounts of AMS, exits the second catalyst bed 126, along with unreacted hydrogen and collect in collection space 128. Hydrogen gas exits via a gas outlet to line 166, and liquid cumene product exit the collection space 128 via filter 168, connected to line 170.

Hydrogenation in the second catalyst bed of any AMS remaining in the cumene feed stream can be between 85 and 100 weight percent of the AMS contained in the feed to the second bed, desirably at least 95 weight percent. AMS content in the product stream from the second catalyst bed 126 can be less than 750 ppmw, desirably less than 300 ppmw.

Hydrogen gas exits via line 166, which can include a valve 172, into drum 174. Cumene product exits via line 170, which can include valve 176, into drum 174. Drum 174 can separate cumene product from volatile light compounds and hydrogen gas, which exit via line 178. Line 178 can include overhead condenser 180, which can condense and return liquid to the drum 174. Gas exits the top of the overhead condenser via line 181, which can include pressure control valve 182, and enters knock out drum 184. Gas from knockout drum 184 can be supplied via line 186 to an incinerator (not shown), purged, processed for hydrogen recovery, used as fuel, or the like.

Cumene product in drum 174 is separated from water and any heavier compounds present and exits via line 188, which can include a pump 190 for delivery of the liquid cumene. The cumene product can be recycled as a circulation stream via line 192, which can include a flow control valve, and can be supplied to line 142. Line 192 can include a bypass line 194, which can supply a portion of the cumene circulation stream to the second reaction zone 114 via line 158. Cumene product exits via line 195, which can include a valve and a heat exchanger 196, and can be supplied to the phenol synthesis loop as feedstock.

Upon start up of the hydrogenation process, the reactor 110 is initially primed with a steady stream of cumene, supplied to the reactor feed line 142 via line 192. The start-up cumene stream can be a recycle stream from the hydrogenation reactor 110, or it can be a portion of the cumene feed stream supplied from the phenol synthesis process. The start-up stream can be continuously supplied to both the first and second reaction zones 112, 114, as a circulation stream.

The reactor pressure can be maintained between 0.2 and 7 MPa (35 and 1015 psia), desirably between 0.3 and 1 MPa (50 and 150 psia). The reactor pressure can be conveniently controlled through the addition of hydrogen. The reactor temperature can be maintained between 16° and 260° C. (60° and 500° F.), desirably between 60° and 90° C. (140° and 194° F.). The reactor can optionally employ heat exchangers within the feed stream to control the temperature of the reaction by varying the temperature of the feed stream. As the nickel catalyst activity decreases, heating of the feed stream may be necessary. Additionally, if desired, cooled product effluent can be recycled as a circulation feed stream via line 192 to control the temperature rise across the reactor as the exothermic reaction progresses.

Residence time for the cumene/AMS feed is generally shorter in the nickel catalyst bed than in the noble metal catalyst bed. The nickel catalyst generally exhibits a higher activity than the noble metal catalysts, and prolonged exposure of the AMS to the nickel catalyst can lead to hydrogenation of the aromatic ring, whereas the noble metal catalysts generally exhibit a higher selectivity to hydrogenation of the ethylenic side chain. The liquid hourly space velocity (LHSV) of the cumene/AMS over the nickel catalyst in the first catalyst bed can be from 10 to 20 $hr^{-1}$, desirably from 12 to 16 $hr^{-1}$. The LHSV of the cumene/AMS over the noble metal catalyst in the second catalyst bed can be from 5 to 15 $hr^{-1}$, desirably from 6 to 12 $hr^{-1}$.

EXAMPLE 1

The following example was conducted in a pilot plant having a reactor with an internal diameter of 21 mm. The pilot plant had a single catalyst bed which consisted of silicon carbide and a nickel catalyst, wherein the catalyst had a volume of 35 mL. The reactor was designed to operate at a pressure between 0.1 and 1 MPa (15 and 150 psia), and a temperature between 50° and 70° C. (122° and 158° F.). The reactor, having a trickle bed with a nickel catalyst having a 16 percent by weight metal content, a trilobe shape and a surface area of 112 $m^2/g$, was operated at 0.7 MPa (100 psia) and 70° C. (158° F.), with an LHSV of 16 $hr^{-1}$. The feed stream consisted of approximately 96 weight percent cumene and approximately 4 weight percent AMS, and was supplied to the reactor where it combined with hydrogen present in an excess of 10-30%. Hydrogenation of the AMS to cumene was approximately 85 percent, with side product isopropylcyclohexane present in a concentration of 34 ppm.

EXAMPLE 2

A hydrogenation reaction according to a reactor described in example 1 is given. The reactor employed a trickle bed with a nickel hydrogenation catalyst with a 16 percent by weight metal content, a trilobe shape, and a surface area of 112 $m^2/g$, was operated at 0.5 MPa (72 psia) and 50° C. (122° F.), with an LHSV of 12 $hr^{-1}$. The feed stream, consisting of approximately 96 weight percent cumene and approximately 4 weight percent AMS, was supplied to the reactor where it combined with a 10-30% excess of hydrogen. Hydrogenation of the AMS to cumene was 99.7 percent, with side product isopropyl cyclohexane present in a concentration of approximately 43 ppm.

EXAMPLE 3

Hydrogenation of a cumene/AMS feed in a reactor having a two catalyst system is given. A cumene/AMS feed comprising 50 weight percent AMS was supplied at a rate of 1000 kg/hr. Hydrogen was added to the cumene/AMS feed at a rate of 100 $Nm^3$/hr. A cumene diluent stream, recycled from the product stream, was added to the feed stream at a rate of 10,000 kg/hr, resulting in a feed to the reactor that contained approximately 5 weight percent AMS. The first reactor included a nickel catalyst having a volume of 1.06 $m^3$. The feed was supplied to the reactor at an LHSV of 12 $hr^{-1}$, and at a temperature that varied from 45° C. (113° F.) at the start of the reaction to 100° C. (212° F.) at the end of the reaction. The reactor was operated at 0.4 MPa (60 psia) at the start of the reaction and 0.8 MPa (120 psia) at the end of the reaction. The product was produced at a rate of 1008 kg/hr and consisted of 0.5 weight percent AMS, corresponding to the hydrogenation of 88.2 percent of the initial AMS feed in the first catalyst bed. The temperature varied from 65° C. (149° F.) at the start of the reaction to 119° C. (246° F.) at the end of the reaction.

The product stream from the first catalyst bed, having an AMS content of approximately 0.5 weight percent, was supplied to the second reactor at a rate of 1008 kg/hr. Hydrogen was added at a rate of 10 Nm$^3$/hr. The second reactor included a trickle bed having 0.13 m$^3$ of a palladium hydrogenation catalyst. The feed was supplied to the reactor at an LHSV of 9 hr$^{-1}$, and a temperature that varied from 60° C. (140° F.) at the beginning of the reaction and 100° C. (212° F.) at the end of the reaction. The reactor was operated at a pressure of between 0.4 MPa (60 psia) at the start of the reaction, and 0.8 MPa (120 psia) at the end of the reaction. Cumene product was produced at a rate of 1008 kg/hr, and had an AMS content of approximately 0.02 weight percent, corresponding to the hydrogenation of 95.4 percent of the AMS supplied to the second reactor, and an overall hydrogenation of 99.9 percent of the initial AMS feed. Side product isopropylcyclohexane (IPCH) concentration in the product stream was no greater than 50 ppmw. Material balances for the first and second catalyst sections are given in Tables 1 and 2 respectively.

TABLE 1

Material Balance for Reactor (First Catalyst Bed).

| Component | Net Feed (kg/hr) | Bed 1 Feed (kg/hr) | Bed 1 Feed (kg/kg) | H2 Feed (kg/hr) | Bed 1 Total Out (kg/hr) | Net Bed 1 Liquid Out | Bed 1 Output (%) | Bed 1 Conv. (%) |
|---|---|---|---|---|---|---|---|---|
| H2 | — | — | — | 10 | 2 | — | — | — |
| AMS | 500 | 550 | 5 | — | 55 | 5 | 0.5 | 85 |
| Cumene | 500 | 10450 | 95 | — | 10,952 | 1,003 | 99.5 | — |
| Total | 1,000 | 11,000 | 100 | 10 | 11,009 | 1,008 | 100 | — |

TABLE 2

Material Balance for Reactor (Second Catalyst Bed).

| Component | Bed 2 Feed (kg/hr) | Bed 2 Feed (kg/kg) | Bed 2 H2 (kg/hr) | Bed 2 Output (kg/hr) | Bed 2 Conv. (%) | Overall Conv. (%) |
|---|---|---|---|---|---|---|
| H2 | — | — | 1.0 | — | — | — |
| AMS | 5 | 0.5 | — | 0.2 | 95.4 | 99.9 |
| Cumene | 1,003 | 99.5 | — | 1,008.3 | — | — |
| Total | 1,008 | 100 | 1.0 | 1,008.5 | — | — |

EXAMPLE 4

In this example, the hydrogenation reactor consists of a vessel having a diameter of approximately 0.85 m and a height of approximately 8 m. The reactor includes two catalyst beds arranged in series in the same reactor shell. The reactor consists of a distributor section which supplies a cumene/AMS feed and hydrogen to a first catalyst bed consisting of a trickle bed having a length of approximately 2.5 m, an L/D of 3, and containing a nickel based catalyst. The cumene/AMS is supplied to the first catalyst bed at an LHSV of 12-16 hr$^{-1}$. The product effluent is supplied to a second distributor which mixes the first catalyst bed effluent with hydrogen gas, and supplies the mixture to a second catalyst bed. The second catalyst bed is a trickle bed having a length of approximately 0.88 m, with an L/D of between 1 and 3, and containing a palladium based hydrogenation catalyst. The product stream from the first catalyst bed is supplied at an LHSV of 8-12 hr$^{-1}$. The reactor also includes an empty volume located below the second catalyst bed to allow for retrofitting of the reactor if desired.

The invention is described above in reference to specific examples and embodiments. The metes and bounds of the invention are not to be limited by the foregoing disclosure, which is illustrative only, but should be determined in accordance with the full scope and spirit of the appended claims. Various modifications will be apparent to those skilled in the art in view of the description and examples. It is intended that all such variations within the scope and spirit of the appended claims be embraced thereby.

What is claimed is:

1. A process for selective hydrogenation of alpha-methylstyrene (AMS) to cumene, comprising:
   contacting a feed stream comprising AMS in cumene with nickel in the presence of hydrogen in a first fixed bed catalytic reaction zone to convert from 70 to 95 percent of the AMS to cumene;
   contacting effluent from the first zone with a noble group metal in the presence of hydrogen in a second fixed bed catalytic reaction zone to convert AMS in the first zone effluent to obtain a net reactor effluent comprising cumene essentially free of AMS.

2. The process of claim 1 wherein the cumene feed stream comprises up to 6 percent AMS by weight.

3. The process of claim 1 wherein the nickel in the first catalytic reaction zone is fixed on an inert support.

4. The process of claim 1 comprising recirculating a portion of the first zone cumene effluent to the cumene feed stream optionally with cooling for temperature control of the first zone.

5. The process of claim 1 comprising supplying the hydrogen to the first reaction zone at a molar hydrogen:AMS ratio of from stoichiometric to 100 percent excess hydrogen.

6. The process of claim 5 wherein unreacted hydrogen is passed from the first reaction zone to the second reaction zone.

7. The process of claim 1 wherein the beds of the first and second reaction zones are disposed in a common reactor vessel.

8. The process of claim 1 wherein the first reaction zone has a liquid hourly space velocity from 10 to 20 per hour.

9. The process of claim 1 wherein the second reaction zone comprises supported palladium catalyst and has a liquid hourly space velocity of from 5 to 15 per hour.

10. The process of claim 1 wherein the first reaction zone has an average temperature between 60° and 90° C.

11. The process of claim 1 wherein the first zone effluent is essentially free of isopropylcyclohexane.

12. The process of claim 1 wherein the first zone effluent comprises less than 50 ppm isopropylcyclohexane.

13. The process of claim 1 wherein the net reactor effluent comprises less than 750 ppmw AMS.

14. The process of claim 1 wherein the net reactor effluent comprises less than 300 ppmw AMS.

15. In a process comprising selective hydrogenation of AMS in a feed stream comprising up to 6 weight percent AMS in cumene over a supported noble group metal catalyst in the presence of hydrogen to obtain a cumene product comprising less than 750 ppmw AMS, the improvement comprising:
 contacting the feed stream in the presence of hydrogen with supported nickel catalyst in a fixed bed upstream from the supported noble group metal catalyst to convert from 70 to 95 percent of the AMS to cumene in an intermediate stream;
 supplying the intermediate stream with hydrogen to a downstream fixed bed comprising the supported noble group metal catalyst to obtain a stream of the cumene product.

16. The improvement of claim 15 comprising recirculating a portion of the intermediate stream to the feed stream optionally with cooling for temperature control of the upstream fixed bed.

17. The improvement of claim 15 comprising supplying the hydrogen to the upstream fixed bed at a molar ratio to the AMS in the feed stream from stoichiometric to 100 percent excess hydrogen.

18. The improvement of claim 17 wherein unreacted hydrogen is passed from the upstream fixed bed to the downstream fixed bed.

19. The improvement of claim 15 wherein the upstream and downstream fixed beds are disposed in a common reactor vessel.

20. The improvement of claim 15 wherein the upstream bed has a liquid hourly space velocity from 10 to 20 per hour.

21. The improvement of claim 15 wherein the downstream bed comprises supported palladium catalyst and has a liquid hourly space velocity of from 5 to 15 per hour.

22. The improvement of claim 15 wherein the upstream bed has an average temperature between 60° and 90° C.

23. The improvement of claim 15 wherein the intermediate stream is essentially free of isopropylcyclohexane.

24. The improvement of claim 15 wherein the intermediate stream comprises less than 50 ppm isopropylcyclohexane.

25. Apparatus for selective hydrogenation of alpha-methyl-styrene (AMS) to cumene, comprising:
 reactor means for contacting a feed stream comprising AMS in cumene with nickel in the presence of hydrogen in a first fixed bed catalytic reaction zone for converting from 70 to 95 percent of the AMS to cumene;
 reactor means for contacting effluent from the first zone with a noble group metal in the presence of hydrogen in a second fixed bed catalytic reaction zone to convert AMS in the first zone effluent for obtaining a net reactor effluent comprising cumene essentially free of AMS.

* * * * *